United States Patent
Gudeman

(10) Patent No.: US 9,745,269 B2
(45) Date of Patent: Aug. 29, 2017

(54) SUPERCRITICAL FLUID EXTRACTION OF BIS-BENZYL ISOQUINOLINES

(71) Applicant: CBA Pharma, Inc., Lexington, KY (US)

(72) Inventor: Beth D. Gudeman, Lexington, KY (US)

(*) Notice: Subject to any disclaimer, the term of this patent is extended or adjusted under 35 U.S.C. 154(b) by 0 days.

(21) Appl. No.: 14/206,810

(22) Filed: Mar. 12, 2014

(65) Prior Publication Data

US 2015/0073151 A1 Mar. 12, 2015

Related U.S. Application Data

(60) Provisional application No. 61/791,648, filed on Mar. 15, 2013.

(51) Int. Cl.
*C07D 217/04* (2006.01)
*C07D 221/12* (2006.01)
*B01D 15/40* (2006.01)

(52) U.S. Cl.
CPC ......... *C07D 217/04* (2013.01); *C07D 221/12* (2013.01); *Y02P 20/544* (2015.11)

(58) Field of Classification Search
None
See application file for complete search history.

(56) References Cited

U.S. PATENT DOCUMENTS

| | | | |
|---|---|---|---|
| 5,119,835 A | 6/1992 | Heemann et al. | |
| 5,302,611 A | 4/1994 | Keplinger et al. | |
| 5,750,709 A | 5/1998 | Castor | |
| 6,113,907 A | 9/2000 | Khwaja et al. | |
| 6,218,541 B1 | 4/2001 | Wang | |
| 6,335,044 B1 | 1/2002 | Wasche et al. | |
| 6,503,396 B2 | 1/2003 | Kim et al. | |
| 6,503,532 B1 | 1/2003 | Murty et al. | |
| 6,746,695 B1 | 6/2004 | Martin et al. | |
| 2004/0018251 A1 | 1/2004 | Koch et al. | |
| 2005/0250725 A1 | 11/2005 | Price et al. | |
| 2006/0195934 A1 | 8/2006 | Apuya et al. | |
| 2007/0027181 A1 | 2/2007 | Nakajima et al. | |
| 2011/0105755 A1 | 5/2011 | Carroll | |

FOREIGN PATENT DOCUMENTS

| | | |
|---|---|---|
| WO | 02051812 | 7/2002 |
| WO | 2004016277 | 2/2004 |
| WO | 2011056965 | 5/2011 |

OTHER PUBLICATIONS

Schiff, Journal of Natural Products, vol. 54, No. 3, pp. 645-749 (May-Jun. 1991).*
Xiao et al, European Food Research and Technology, vol. 231, pp. 407-414 (May 16, 2010).*
"Feasibility Assessment for Supercritical Fluid Extraction of CBT-1 from Four Different Samples Supplied by CBA," Final Report Addendum Jun. 8, 2005, Murty Pharmaceuticals, Inc., by Ram Murty, Ph.D.
Feasability Assessment for Supercritical Fluid Extraction of CBT-1 from Four Different Samples Supplied by CBA, Final Report May 27, 2005, Murty Pharmaceuticals, Inc., by Ram Murty, Ph.D.

* cited by examiner

*Primary Examiner* — Zinna Northington Davis
(74) *Attorney, Agent, or Firm* — Mitchell Intellectual Property Law, PLLC

(57) ABSTRACT

An improved process for obtaining at least one bis-benzyl isoquinoline alkaloid from botanical material involves contacting the botanical material with a supercritical fluid having as a major component one or more aliphatic hydrocarbon compounds, such as alkanes, alkenes, cyclic aliphatic hydrocarbons, or a combination of these compounds.

7 Claims, No Drawings

SUPERCRITICAL FLUID EXTRACTION OF BIS-BENZYL ISOQUINOLINES

CROSS REFERENCE TO RELATED APPLICATIONS

The present application claims the benefit of U.S. Provisional Patent Application No. 61/791,648, entitled SUPERCRITICAL FLUID EXTRACTION OF BIS-BENZYL ISOQUINOLINES, filed on Mar. 15, 2013, the entire contents of which are incorporated by reference.

FIELD OF THE INVENTION

This invention relates to the field of separating specific compounds from a botanical material containing a combination of compounds.

SUMMARY OF THE INVENTION

It has been discovered that improved separation of certain bis-benzyl isoquinolines from botanical materials may be achieved using supercritical solvent extraction. The preferred improved process involves extracting the bis-benzyl isoquinolines tetrandrine and ethylfangchinoline from *Stephania Tetrandra* by contacting this botanical material with a supercritical fluid comprised primarily of an aliphatic hydrocarbon.

These and other features, advances and objects of the present invention will be further understood and appreciated by those skilled in the art by reference to the following specification and claims.

DETAILED DESCRIPTION OF PREFERRED EMBODIMENTS

The term "supercritical fluid" refers to a fluid that is above its critical pressure and above its critical temperature. A fluid in the supercritical state exhibits mass transfer characteristics similar to a gas while exhibiting solvating properties similar to a liquid. Thus, a supercritical fluid penetrates material much like a gas, and dissolves materials much like a liquid.

Supercritical solvent extraction involves contacting a first material with a supercritical fluid for a time sufficient to cause one or more components of the first material to separate from the first material and dissolve in the supercritical fluid, and thereafter separating the component or components from the supercritical fluid. A complete separation of the extended components from the supercritical fluid is typically achieved by a temperature and/or pressure change.

Supercritical fluid extraction in accordance with the preferred embodiments can be performed as a batch extraction, as a continuous cascading extraction, as a countercurrent solvent extraction, or a combination thereof. The majority of supercritical fluid extractions are batch loaded systems. In these systems, extraction vessels are loaded with raw material, sealed, and the pressure and temperature increased to the desired supercritical process conditions. After extraction is completed, the pressure and temperature are decreased, the vessel opened, and the spent raw material is removed before the process can be repeated. In a continuous cascading extraction, multiple extraction vessels are sequentially entered on-line in a continuous manner, with the supercritical fluid passing from vessel to vessel, collecting specific targeted compounds in each vessel. In a countercurrent extraction process, bioactive substances from plants and herbs are extracted and concentrated in a series of countercurrent mechanical presses. The presses can be kept at high pressure and escalated temperature to facilitate supercritical fluid extraction. Supercritical fluid extraction units are commercially available.

Because the supercritical fluids used in the extraction processes of the invention are comprised primarily of one or more aliphatic hydrocarbons, which are flammable and potentially explosive, the extraction unit and other equipment used for practicing the invention should be explosion proof.

In the preferred embodiment, *Stephania Tetrandra* tuber is crushed and/or comminuted and exposed to the aliphatic hydrocarbon in its super critical condition. Examples of hydrocarbon solvents that may be utilized include alkanes such as ethane and propane, alkenes such as ethylene and propylene, and cyclic aliphatic hydrocarbons such as cyclohexane. A preferred aliphatic hydrocarbon is propane.

The supercritical fluids used in the extraction processes of this invention consist essentially of, or are comprised primarily of, an aliphatic hydrocarbon. The term "consisting essentially of an aliphatic hydrocarbon" means that the supercritical fluid contains one or more aliphatic hydrocarbons, and may contain small or incidental amounts of other fluids that do not have an appreciable effect on the extraction process. The term "comprised primarily of an aliphatic hydrocarbon" means that the supercritical fluid comprises more than 50% (by volume) of one or more aliphatic hydrocarbons.

Although not necessary to achieve commercially viable exaction, it may be desirable in some cases to utilize a one or more cosolvents in a minor amount (i.e., less than 50% by volume). Examples of cosolvents include acetonitrile, alcohols such as methanol and ethanol and halogenated hydrocarbons such as chloroform, chlorotrifluoromethane, and trichlorofluoromethane. Methanol is most preferred.

It has been determined that the process of this invention is especially useful for isolating and/or purifying tetrandrine and ethylfangchinoline from *Stephania Tetrandra* tuber. While tetrandrine and ethylfangchinoline do not appreciably migrate into supercritical carbon dioxide, these compounds surprisingly substantially completely migrate into supercritical propane. In the case of pure or substantially pure propane, the appropriate extraction conditions are at a temperature above the critical temperature (i.e., above 369.8° k) and a pressure above the critical pressure (i.e., above 42.5 bar).

It has been determined that tetrandrine and ethylfangchinoline extracted from *Stephania Tetrandra* Tubers using supercritical propane and recovered by subsequent evaporation of the propane do not undergo any degradation. More specifically, chromatography techniques did not reveal any degradation products of tetrandrine or ethylfangchinoline.

Of course, it is understood, that the forgoing are preferred embodiments of the invention, and that variations can be employed without departing from the spirit of the invention as set forth in the appended claims, interpreted in accordance with the principles of patent law.

The invention claimed is:

1. A process for extracting tetrandrine and/or ethylfangchinoline from *Stephania Tetrandra* plant material, comprising: contacting the *Stephania Tetrandra* plant material with a supercritical fluid comprised primarily of at least one aliphatic hydrocarbon.

2. The process of claim 1, wherein the at least one aliphatic hydrocarbon compound is selected from the group consisting of alkanes, alkenes, cyclic aliphatic hydrocarbons, and combinations of these compounds.

3. The process of claim 1, wherein the at least one aliphatic hydrocarbon is an alkane.

4. The process of claim 1, wherein the at least one aliphatic hydrocarbon is propane.

5. The process of claim 1, wherein the supercritical fluid includes a cosolvent.

6. The process of claim 5, wherein the cosolvent is selected from alcohols and halogenated hydrocarbons.

7. The process of claim 5, wherein the cosolvent is methanol.

\* \* \* \* \*